(12) United States Patent
Sugiyama et al.

(10) Patent No.: US 6,660,142 B2
(45) Date of Patent: Dec. 9, 2003

(54) NONFRAGILE AND QUICKLY ACTIVATABLE STRUCTURE OF GAS SENSOR ELEMENT

(75) Inventors: Tomio Sugiyama, Nagoya (JP); Makoto Nakae, Toyoake (JP); Shinichiro Imamura, Kariya (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 09/994,052

(22) Filed: Nov. 27, 2001

(65) Prior Publication Data

US 2002/0063059 A1 May 30, 2002

(30) Foreign Application Priority Data

Nov. 30, 2000 (JP) .................................... 2000-365577
Jul. 26, 2001 (JP) .................................... 2001-226451

(51) Int. Cl.$^7$ ............................................. G01N 27/407
(52) U.S. Cl. ......................... 204/408; 204/426; 204/429
(58) Field of Search ........................ 204/408, 421–429

(56) References Cited

U.S. PATENT DOCUMENTS

| 4,224,113 | A | * | 9/1980 | Kimura et al. |
| 4,559,126 | A | | 12/1985 | Mase et al. |
| 4,650,560 | A | | 3/1987 | Ueno |
| 5,700,367 | A | | 12/1997 | Yamada et al. |
| 5,895,591 | A | * | 4/1999 | Kojima et al. |

FOREIGN PATENT DOCUMENTS

| EP | 0331513 A2 | 9/1989 |
| EP | 0667523 A2 | 8/1995 |
| JP | 2-75188 | 3/1990 |

* cited by examiner

Primary Examiner—T. Tung
(74) Attorney, Agent, or Firm—Nixon & Vanderhye PC

(57) ABSTRACT

A nonfragile ad quickly activatable structure of a gas sensor element which may be built in a gas sensor employed in an air-fuel ratio control system for automotive vehicles for measuring the concentration of gas such $O_2$, NOx, or CO. The gas sensor element is made of a lamination of a measurement gas electrode, a reference gas electrode, and a heater. The heater works to elevate the temperature of the gas sensor element up to a given value required to bring the gas sensor element into an activated condition. The heater includes a heater substrate, a heating element, and power supply leads. A minimum distance X between an edge of the heater substrate and an edge of the heating element meets a relation of 0.1 mm$\leq$X$\leq$0.6 mm, thereby minimizing a thermal expansion difference between the heater element and the heater substrate to avoid cracks in a portion of the heater substrate near the heater element. It also becomes possible to elevate the temperature of the heating element up to a higher value, thereby allowing the gas sensor element to be activated quickly immediately after the power is supplied to the heating element.

6 Claims, 10 Drawing Sheets

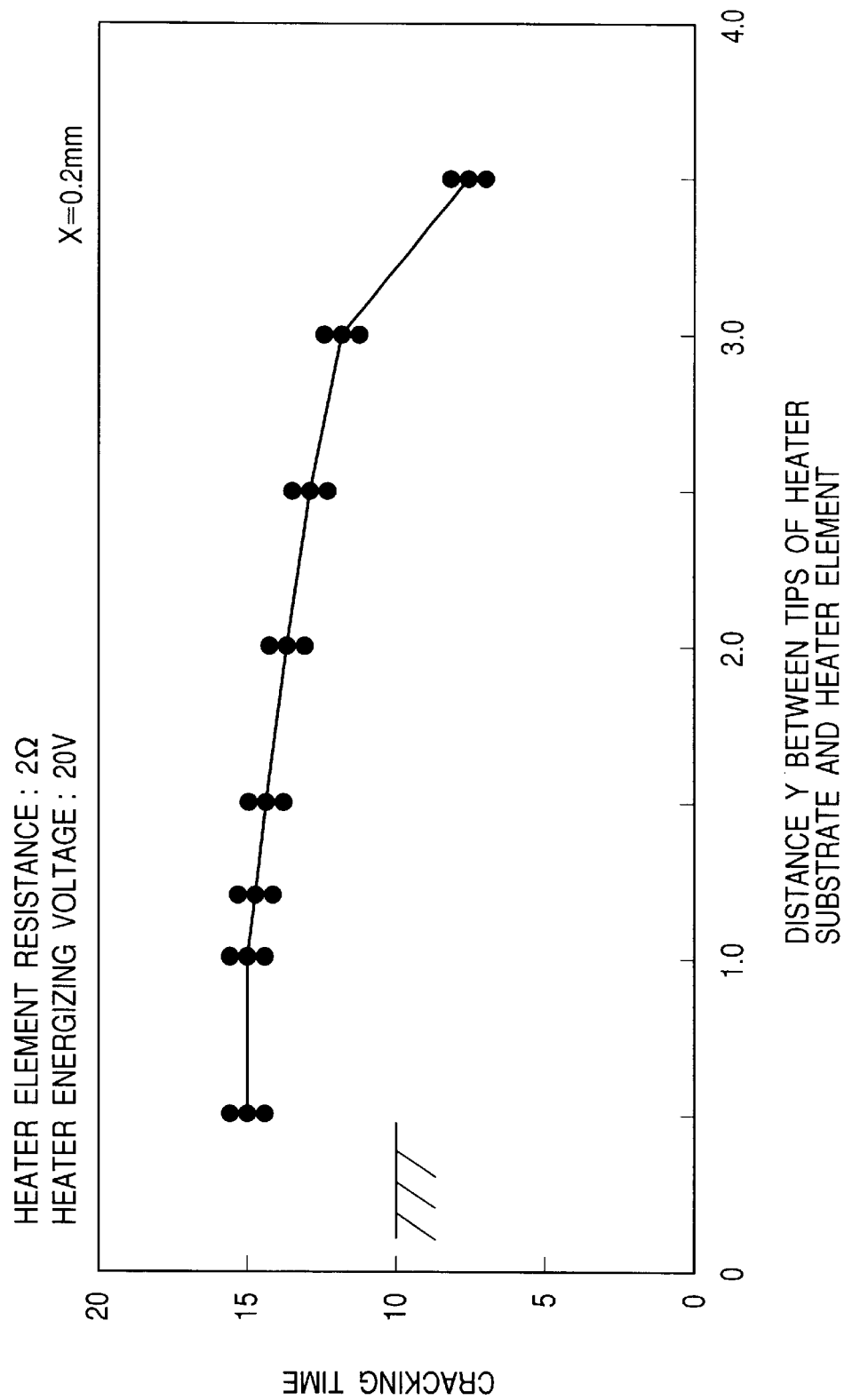

NONFRAGILE AND QUICKLY ACTIVATABLE STRUCTURE OF GAS SENSOR ELEMENT

BACKGROUND OF THE INVENTION

1. Technical Field of the Invention

The present invention relates generally to a gas sensor element which may be built in a gas sensor employed in an air-fuel ratio control system for automotive vehicles for measuring the concentration of gas such $O_2$, NOx, or CO, and more particularly to a nonfragile ad quickly activatable structure of a gas sensor element.

2. Background Art

Typical exhaust systems of automotive engines use a gas sensor for air-fuel ratio control. As such, there are known ones which consist of a solid electrolyte body having oxygen-ion conductivity, a measurement gas electrode exposed to a gas to be measured, and a reference gas electrode exposed to a reference gas. The measurement gas electrode and the reference gas electrode are installed on the solid electrolyte body. An oxygen-ion current is produced which flows through the measurement and reference gas electrodes and is used for determining the air-fuel ratio.

In recent years, there is an increasing need for speeding up an elevation in temperature of a sensor element of the gas sensor and/or reducing the size of the gas sensor in order to shorten the active time required for the gas sensor to start to produce a correct output and enable the gas sensor to be mounted in various places (e.g., in an exhaust pipe beneath a floor of a vehicle body).

To meet the above requirements, gas sensors equipped with a heater have become employed.

In recent years, the activation time of gas sensors is required to be shortened further in order to enhance the performance of a three way catalytic converter to convert polluting exhaust gasses into harmless products immediately after the startup of the engine.

However, an increase in temperature of the heater for achieving the quick activation of the sensor element will cause a great thermal stress to act on a portion of a body of the sensor element near the heater, thus resulting in formation of cracks in the body of the sensor element.

In order to avoid the above drawback, Japanese Patent First Publication No. 2-75188 teaches a heater which is so designed as to meet a relation of $0.7X \leq Y \leq 1.5X$ where X is a minimum distance between a side of a heater substrate and a side of a heater element, and Y is a minimum distance between a tip of the heater substrate and a tip of the heater element. Use of a heater having such dimensions serves to decrease cracks in a top portion of the sensor element, but does not avoid cracks in side portions thereof.

SUMMARY OF THE INVENTION

It is therefore a principal object of the present invention to avoid the disadvantages of the prior art.

It is another object of the present invention to provide a gas sensor element which is capable of being activated fast and nonfragile in structure.

According to one aspect of the invention, there is provided a gas sensor element which may be built in a gas sensor for measuring the concentration of gas such $O_2$, NOx, or CO used in an air-fuel ratio control system of automotive vehicles. The gas sensor element comprises: (a) a solid electrolyte member having opposed surfaces; (b) a measurement gas electrode disposed on one of the opposed surfaces of the solid electrolyte member, the measurement gas electrode being exposed to a gas to be measured; (c) a reference gas electrode disposed on the other of the opposed surfaces of the solid electrolyte member, the reference gas electrode being exposed to a reference gas; and (d) a heater laminated on the solid electrolyte member. The heater includes a heater substrate, a heating element, and leads for supplying power to the heating element. The heating element and leads are disposed on the heater substrate. A minimum distance X between an edge of the heater substrate and an edge of the heating element is so set as to meet a relation of $0.1 \text{ mm} \leq X \leq 0.6 \text{ mm}$.

If the distance X is less than 0.1 mm, it becomes difficult to ensure an interval between the heating substrate and the heating element required for establishing desired electric insulation therebetween. This causes the current flowing through the heating element to leak to the measurement gas and reference gas electrodes and a portion of the solid electrolyte member near the electrodes, which may result in an error in measuring the concentration of the gas. Alternatively, if the distance X is greater than 6.0 mm, it may result in an increase in thermal stress when the gas sensor element is heated quickly which causes cracks to occur in, for example, the heater substrate.

In the preferred mode of the invention, the heater substrate and the heating element each have a length. A minimum distance Y between a tip of the heater substrate and a tip of the heating element is so set as to meet a relation of $1.0 \text{ mm} \leq Y \leq 2.5 \text{ mm}$. This serves to decrease a difference in temperature or thermal expansion between the heating element and a portion of the heater substrate near the heating element, thereby ensuring a desired resistance to cracks. It also becomes possible to elevate the temperature of the heating element up to a higher value, thereby allowing the gas sensor element to be activated quickly after the power is supplied to the heating element.

A reference gas chamber is defined in the gas sensor element into which the reference gas is admitted and to which the reference gas electrode is exposed. The reference gas chamber has a length substantially coinciding with a length of the heating element, and a width A of the reference gas chamber and a width B of the heating element meet a relation of A<B. This dimensional limitation allows a projected area of the reference gas chamber to be included in a projected area of the heating element, thereby resulting in ease of transmission of heat from the heating element to the reference gas chamber. This decreases a difference in temperature between the measurement gas electrode, the reference gas electrode, and a portion of the solid electrolyte member near the electrodes, thereby avoiding occurrence of cracks in the gas sensor element.

The gas sensor element has a width of 3 mm to 6 mm. This results in an increased resistance of the gas sensor element to cracks due to thermal shocks and enables the pattern of the heating element which is excellent in heating efficiency to be designed.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 6 is a graph which represents a relation between a time until cracking and a distance Y between tips of a heater substrate and a heating element;

DESCRIPTION OF THE PREFERRED EMBODIMENTS

Figure 1:
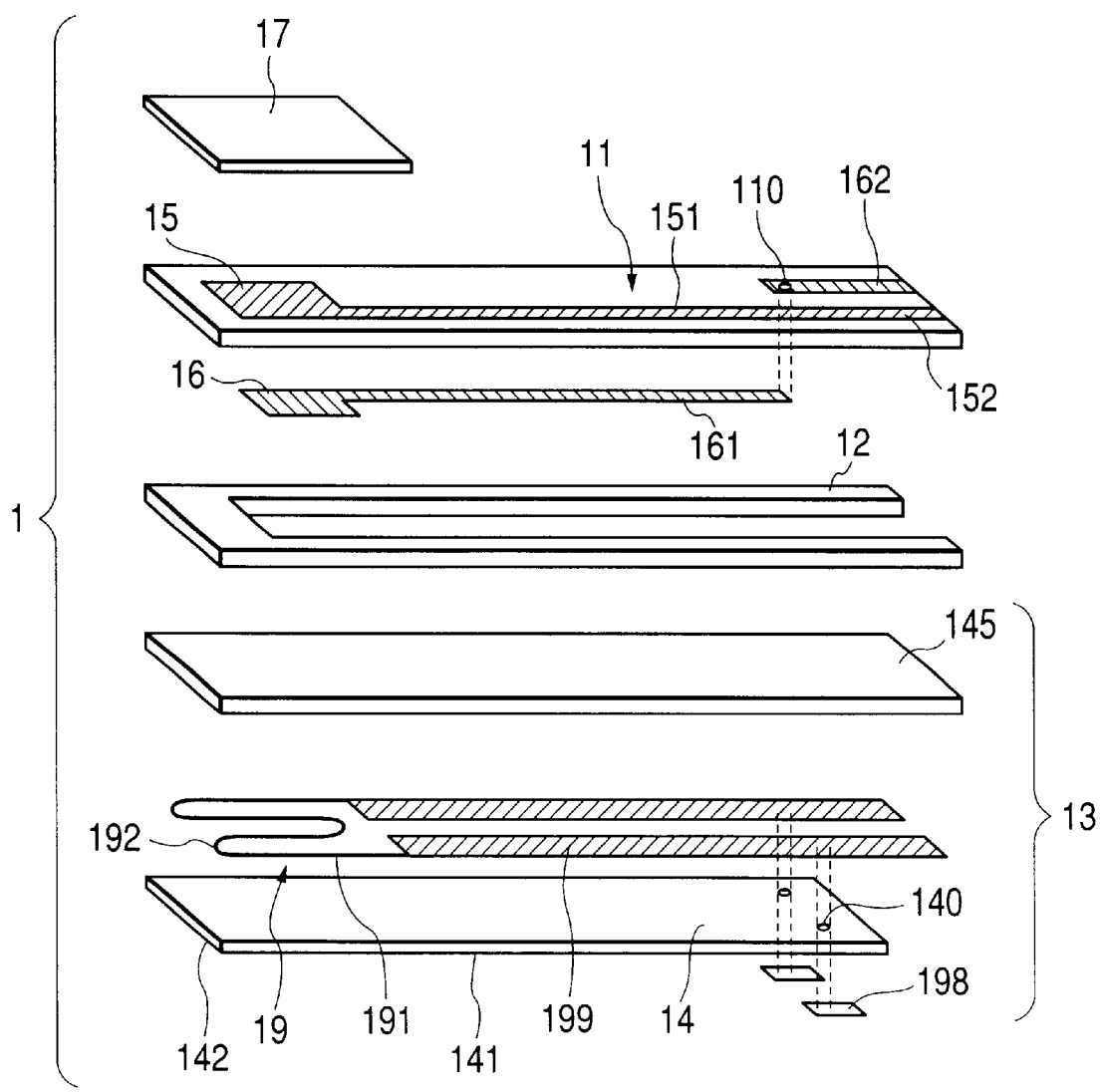
FIG. 1 is an exploded perspective view which shows a gas sensor element according to the first embodiment of the invention.

Referring now to the drawings, wherein like numbers refer to like parts in several views, particularly to FIG. 1, there is shown a gas sensor element 1 according to the invention which may be installed in an oxygen sensor employed in automotive air-fuel ratio control systems to measure an oxygen content in exhaust gasses of an internal combustion engine. Note that the present invention is not limited to an oxygen sensor and may alternatively be used with a variety of gas sensors such as HC, CO, NOx, and λ sensors, and single or multi-cell gas sensors equipped with a pump cell. For example, U.S. Pat. No. 5,573,650, issued Nov. 12, 1996 to Fukaya et al., teaches an oxygen sensor equipped with a laminated sensor element, disclosure of which is incorporated herein by reference.

Figure 2:
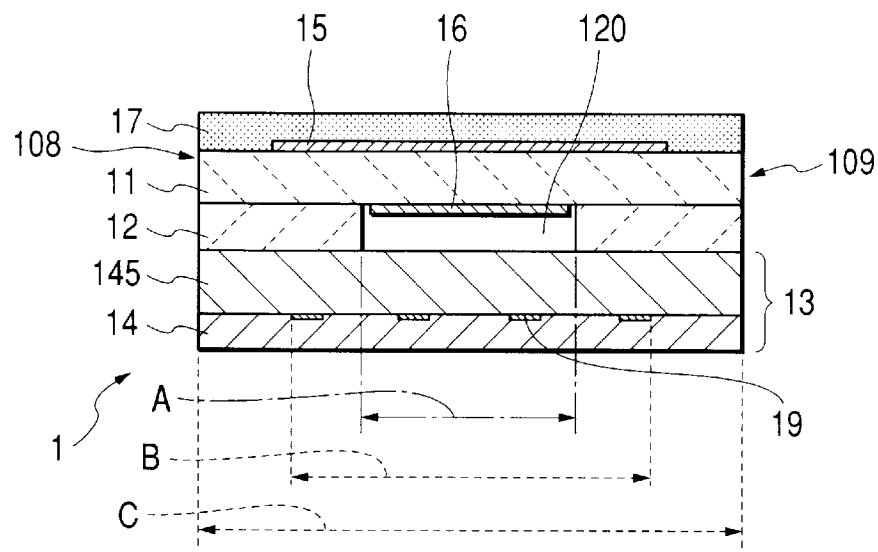
FIG. 2 is a traverse cross section which shows the gas sensor element of FIG. 1.

The gas sensor element 1 is made of a lamination of a solid electrolyte plate 1, a measurement gas electrode 15, a reference gas electrode 16, a spacer 12, and a heater 13 which have lengths oriented in the same direction and longitudinal center lines thereof substantially coinciding with each other. The measurement gas electrode 15 is formed on a surface of the solid electrolyte plate 1 which is exposed to a gas to be measured. The reference gas electrode 16 is formed on an opposite surface of the solid electrolyte plate 1 which is exposed to a reference gas such as air admitted into a reference gas chamber 120, as shown in FIG. 2. The heater 13 is attached to the solid electrolyte plate 11 through the spacer 145.

The heater 13 is made up of a heater substrate 14, power supply leads 199, a heating element 19, and an insulating substrate 145. A minimum distance X between a side edge 141 of the heater substrate 14 and a side edge 191 of the heating element 19 is so set as to meet a relation of 0.1 mm≦X≦0.6 mm. The reason for this dimensional limitation will be described later in detail.

The solid electrolyte plate 11 is made of an oxygen ion conductive material. The spacer 12 is of a tuning fork shape and defines, as shown in FIG. 2, the reference gas chamber 120 between the solid electrolyte plate 11 and the insulating substrate 145. Between the solid electrolyte plate 11 and the spacer 12, $SiO_2$ and $Al_2O_3$ exist. $Al_2O_3$ serves as an anchor to achieve a firm joint of the solid electrolyte plate 11 and the spacer 12.

The measurement gas electrode 15 is, as described above, formed on the outer surface of the solid electrolyte plate 11 and covered with a protective film 17. The reference gas electrode 16 is formed on the inner surface of the solid electrolyte plate 11 and exposed to the reference gas chamber 20. Output pickup leads 151 and 161 and terminals 152 and 162 are formed on the solid electrolyte plate 11 in electric connection with the measurement gas electrode 15 and the reference gas electrode 16, respectively.

Figure 3:
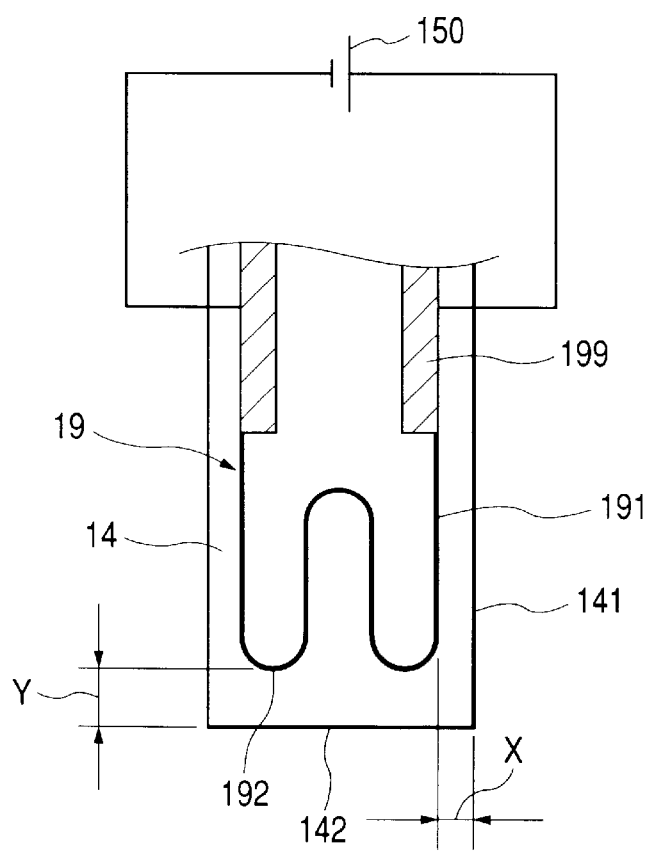
FIG. 3 is a partially enlarged view which shows a heating element disposed on a heater substrate.

The heater 13 includes, as described above, the heating element 19 connected to the power supply leads 199 for applying the voltage to the heating element 19. The power supply leads 199 are connected to a power supply 150, as shown in FIG. 3, through terminals 198. The heating element 19 is, as clearly shown in FIG. 3, made of a conductive string which is narrower than the power supply leads 199 and bent to a W-shape.

In the structure, as illustrated in FIG. 3, the minimum distance X between the side edge 141 of the heater substrate 14 and the side edge 191 of the heating element 19 is 0.2 mm. A minimum distance Y between the tip 192 of the heating element 19 and the end 142 of the heater substrate 14 is 1.2 mm.

A maximum width A of the reference gas chamber 120 is, as clearly shown in FIG. 2, smaller than a width B of the heating element 19. In this embodiment, A is 1.6 mm, and B is 4.1 mm.

A width C of the gas sensor element 1 is equivalent to the distance between the side edges 108 and 109 of a portion of the solid electrolyte plate 11 on which the measurement gas electrode 15 is disposed. In this embodiment, C is 4.5 mm.

A sequence of manufacturing processes of the gas sensor element 1 will be discussed below.

First, a green sheet for making the solid electrolyte plate 11 is prepared in the following manner. Powders of zirconia and yttria having given grain sizes are prepared. From the powders, 94.0 mol % of zirconia and 6.0 mol % of yttria are taken. Next, to this powder mixture, 0.15 parts by weight of $SiO_2$ and 2.0 parts by weight of $Al_2O_3$ per 100 parts by weight of the powder mixture are added and ground in a pot mill for a given period of time. To this flour, a mixture of ethanol and toluene serving as an organic solvent, polyvinylbutyral working as binder, and dibutylphthalate working as plasticizer are added to make slurry.

Next, a zirconia sheet is made of the slurry using the doctor blade. The zirconia sheet has a thickness of 0.2 mm.

The zirconia sheet is cut to a rectangular shape measuring 5 mm×70 mm. A through hole 110 is formed for establishing electric communication between the lead 161 of the reference gas electrode 16 and the terminal 162.

On the zirconia sheet, the measurement gas electrode 15, the reference gas electrode 16, the leads 151 and 161, and the terminals 152 and 162 are formed by the screen printing using a Pt paste to which zirconia is added, thereby forming the green sheet for the solid electrolyte plate 11.

Subsequently, alumina green sheets for making the spacer 12, the insulating substrate 145, and the heater substrate 14 are prepared in the following manner.

Powder of alumina having a given grain size is ground in a pot mill for a given period of time. To this flour, a mixture of ethanol and toluene serving as an organic solvent, polyvinylbutyral working as binder, and dibutylphthalate working as plasticizer are added to make slurry.

Next, an alumina sheet is made of the slurry using the doctor blade. The alumina sheet has a thickness of 0.4 mm.

The alumina sheet is cut into three rectangular sheets measuring 5 mm×70 mm. Of the three sheets, two are used as they are for making the heater substrate 14 and the insulating substrate 145. In the remaining sheet, a slit measuring 2 mm×67 mm is cut for making the spacer 12.

In the alimina sheet produced for the heater substrate 14, through holes 140 are formed for establishing electric communication between the leads 199 and the terminals 198. Next, the heating element 19, the leads 199, and the terminals 198 are formed by the screen printing using a Pt paste to which alumina is added.

A green sheet for making the protective film 17 is prepared in the following manner.

Powder of alumina having a grain size greater than that of the above described material used for making the heater substrate 14 is ground in a pot mill for a given period of time. To this flour, a mixture of ethanol and toluene serving as an organic solvent, polyvinylbutyral working as binder, and dibutylphthalate working as plasticizer are added to make slurry.

Next, an alumina sheet is made of the slurry using the doctor blade which has a thickness of 0.2 mm. The alumina sheet is cut to a rectangular shape measuring 5 mm×30 mm to produce a green sheet for making the protective film 17.

Finally, all the green sheets produced in the above manner are laminated by the thermocompression bonding and baked at 1500° C. for one hour, thereby making the gas sensor element 1 as shown in FIGS. 1 to 3.

We performed tests to evaluate the performance of the gas sensor element 1 in the following manner.

First, samples were prepared which were identical in shape to the gas sensor element 1, but had different minimum distances X. The voltage was applied to the heating element 19 of each sample to heat the sample at a given temperature for one minute. Afterwards, the sample was cooled down to room temperature in two minutes. This thermal shock test was repeated 5000 times. A dyeing test was made to check each sample for cracks. A sequence of these test processes were repeated five times to measure a maximum temperature at which no crack was formed in all the samples. The maximum temperature was defined as a durability temperature.

We also performed insulation resistance tests on the samples in the following manner.

The tip of each sample was put into a water tank. The degree of insulation between the water and the heating element 19 was measured using an insulation resistance tester. The results of the tests are illustrated in FIG. 4.

Figure 4:
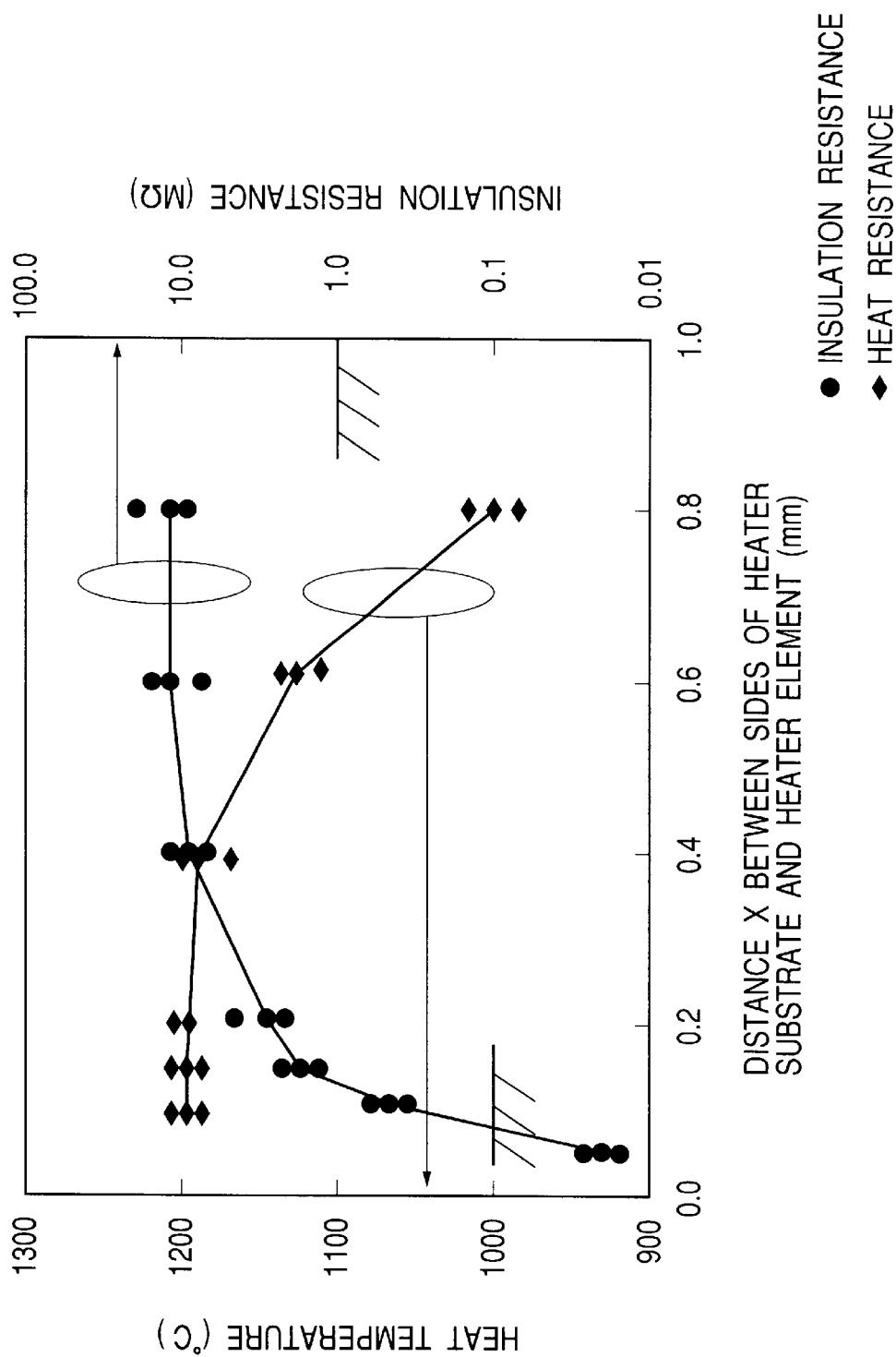
FIG. 4 is a graph which represents a relation between heat temperature and a distance X between side edges of a heater substrate and a heating element and a relation between insulation resistance and the distance X.

FIG. 4 shows that some of the samples meeting the relation of 0.1 mm$\leq$X$\leq$0.6 mm are excellent in heat resistance and insulation resistance, less susceptible to cracks caused by a quick rise in temperature, and are not affected by a current leakage from the heating element 19.

We also performed crack tests on the samples by applying 20V to the heating element 19 for a given period of time and dyeing them to check cracks, thereby determining a limit time until cracks appear. This measurement was made by controlling the resistance of the heating element 19 within a range of 0.1$\Omega$. The results of the test are indicated in FIG. 5.

Figure 5:
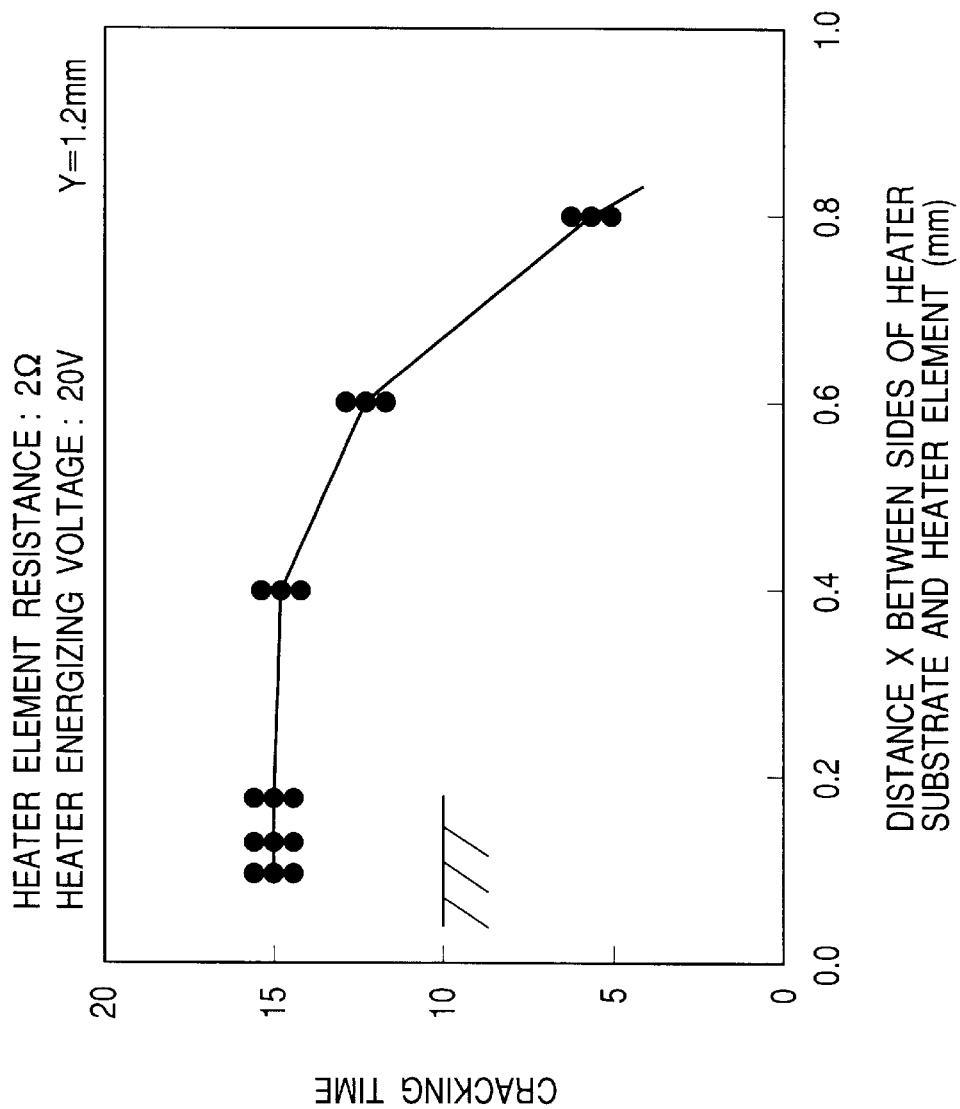
FIG. 5 is a graph which represents a relation between a time until cracking and a distance X between side edges of a heater substrate and a heating element.

FIG. 5 shows that the time until cracks appear in some of the samples meeting the relation of 0.1 mm$\leq$X$\leq$0.6 mm exceeds a target time of 10 minutes (at a heater surface temperature of 1000° C.). It is, therefore, found that the gas sensor element 1 satisfying the relation of 0.1 mm$\leq$X$\leq$0.6 mm will be activated within 10 minutes at a heater surface temperature of 700° C.

Further, we prepared samples having different distances Y between the tip 192 of the heating element 19 and the end 142 of the heater substrate 14 and performed the same tests as described above on the samples. The results of the tests are shown in FIG. 6.

FIG. 6 shows that the time until cracks occur in some of the samples meeting the relation of 1.0 mm$\leq$Y$\leq$2.5 mm exceeds a target time of 10 minutes (at a heater surface temperature of 1000° C.) and that the gas sensor element 1 satisfying the relation of 1.0 mm$\leq$Y$\leq$2.5 mm is excellent in thermal shock resistance.

As already discussed, the gas sensor element 1 is so designed as to satisfy the relations of 0.1 mm$\leq$X$\leq$0.6 mm and 1.0 mm$\leq$Y$\leq$2.5 mm. This serves to decrease a difference in temperature or thermal expansion between the heating element 19 and an adjacent portion of the heater substrate 14, thereby ensuring a desired resistance to cracks. It also becomes possible to elevate the temperature of the heating element 19 up to a higher value, thereby allowing the gas sensor element 1 to be activated quickly immediately after the power is supplied to the heating element 19.

If the minimum distance Y is less than 1.0 mm, it becomes impossible to ensure an interval between the heating element 19 and the heater substrate 14 required for establishing desired electric insulation. This dimensional condition is suitable for avoiding cracks in the heater substrate 14, but will cause a uniformly heated area of the gas sensor element 1 (i.e., the measurement gas and reference gas electrodes 15 and 16 and a portion of the solid electrolyte plate 11 surrounded by the electrodes 15 and 16) to be shifted to the tip of the gas sensor element 1, thereby limiting locations and areas of the electrodes 15 and 16 undesirably. Alternatively, if the minimum distance Y is greater than 2.5 mm, it may result in an increase in thermal stress when the gas sensor element 1 is heated quickly, which leads to occurrence of cracks in the heater substrate 14.

The width A of the reference gas chamber 20 is, as already described, smaller than the width B of the heating element 19, so that a projected area of the reference gas chamber 20 may be included in a projected area of the heating element 19, thereby resulting in ease of transmission of heat from the heating element 19 to the reference gas chamber 20. This decreases a difference in temperature between the measurement gas electrode 15, the reference gas electrode 16, and a portion of the solid electrolyte plate 11 near the electrodes 15 and 16, thus avoiding cracks in the gas sensor element 1.

The width C of the gas sensor element 1 lies within a range of 3 mm to 6 mm, thereby resulting in an increased resistance thereof to cracks due to thermal shocks and enabling the pattern of the heating element 19 which is excellent in heating efficiency to be designed.

Figure 7A:
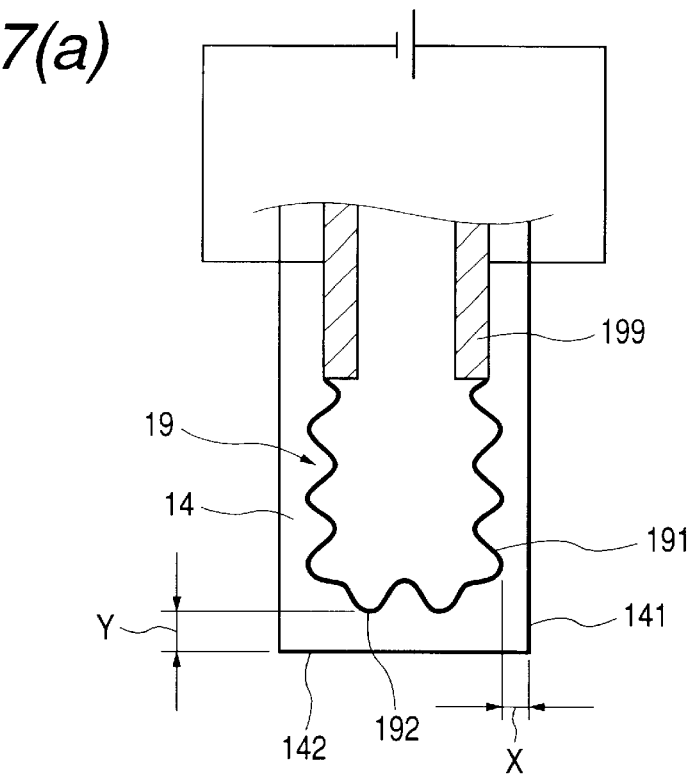
FIGS. 7(a) and 7(b) show modification of a heating element according to the second embodiment of the invention.
Figure 7B:
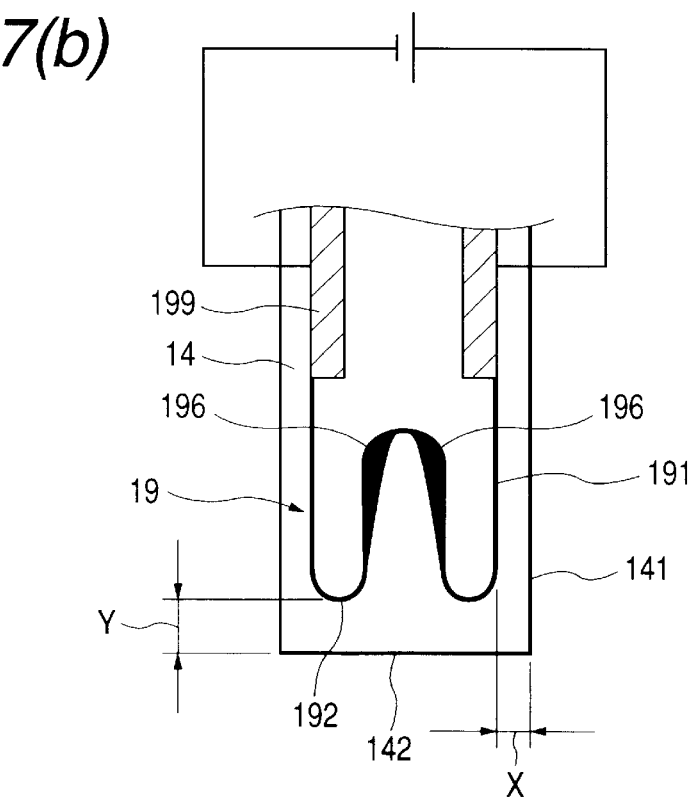

FIGS. 7(a) and 7(b) show modifications of the heating element 19 according to the second embodiment of the invention.

The heating element 19 of FIG. 7(a) is made of a conductive string waved from ends thereof connected to the leads 199 to the tip thereof. In this structure, the distance X is an interval between an outermost side portion 191 of the heating element 19 and the side edge 141 of the heater substrate 14. The distance Y is an interval between an outermost end portion or tip 192 of the heating element 19 and the end 142 of the heating substrate 14.

The heating element 19 of FIG. 7(b) is made of a conductive strip having varying width. Inner side portions, as indicated at 196, of the heating element 19 have the greatest width. Other arrangements are identical with those in the first embodiment, and explanation thereof in detail will be omitted here.

Figure 8:
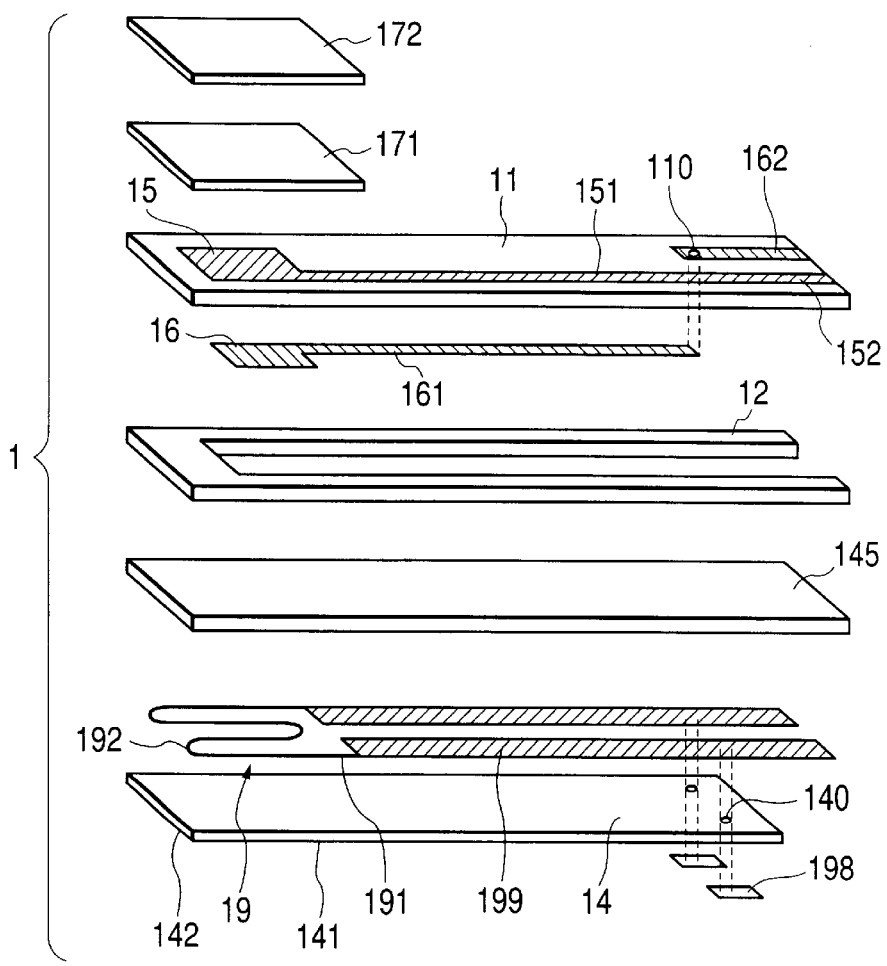
FIG. 8 is an exploded perspective view which shows a gas sensor element according to the third embodiment of the invention.
Figure 9:
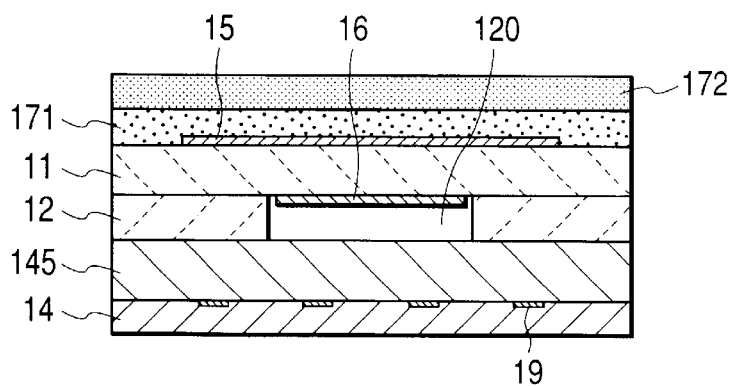
FIG. 9 is a traverse cross section of FIG. 8.

FIGS. 8 and 9 show a gas sensor element 1 according to the third embodiment of the invention which is of a limiting current type.

The gas sensor element 1 has a porous layer 171 and a dense layer 172. The porous layer 171 is disposed on the solid electrolyte plate 11 to cover the measurement gas electrode 15. The dense layer 172 is disposed on the porous layer 171 to cover it. Other arrangements are identical with those in the first embodiment, and explanation thereof in detail will be omitted here.

Figure 10:
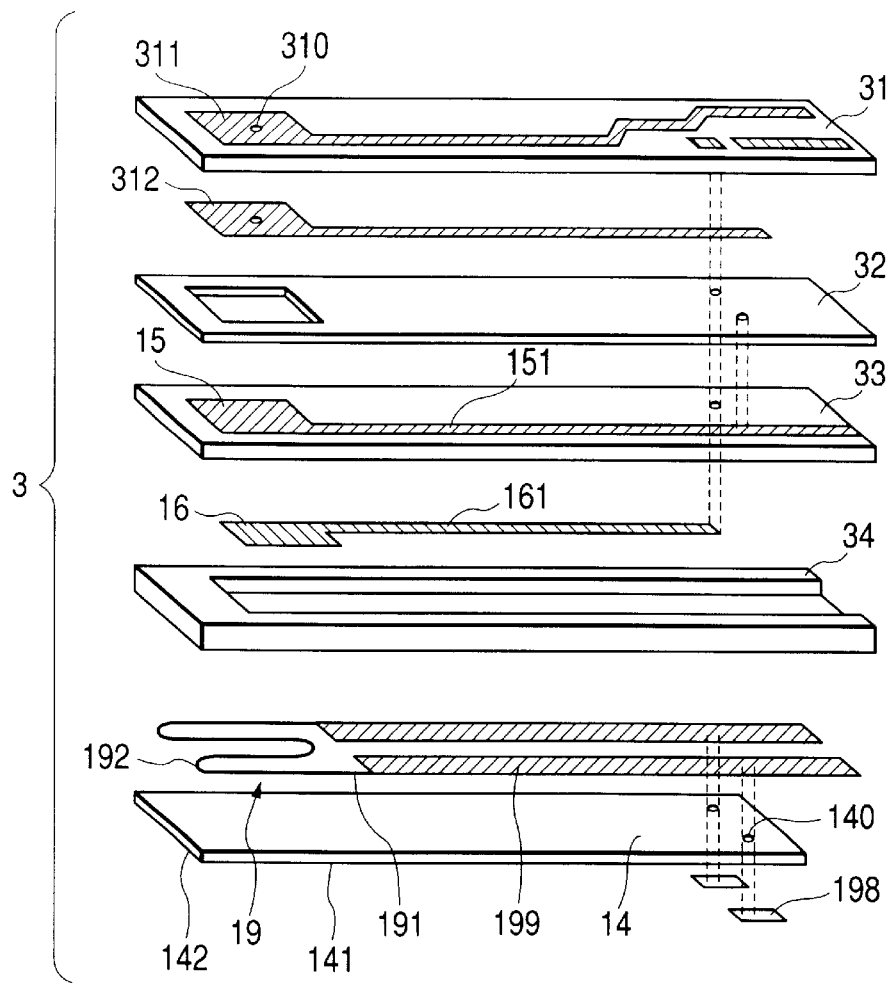
FIG. 10 is an exploded perspective view which shows a gas sensor element according to the fourth embodiment of the invention.
Figure 11:
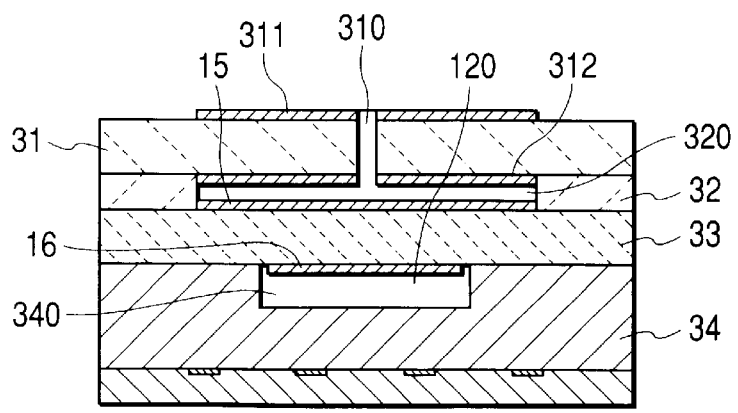
FIG. 11 is a traverse cross section of FIG. 10.

FIGS. 10 and 11 show a gas sensor element 3 according to the fourth embodiment of the invention which is of a two-cell type.

The gas sensor element 3 includes zirconia-based solid electrolyte plates 31 and 33, spacers 32 and 34, and a heater substrate 14 on which a heating element 19 is disposed.

The solid electrolyte plate 31 has a pair of pump electrodes 311 and 312 attached to opposed surfaces thereof. The pump electrodes 311 and 312 have formed therein a pinhole 310 for admitting a gas to be measured into a gas chamber 320.

The spacer 32 is interposed between the solid electrolyte plates 31 and 33 and has an opening to define, as clearly shown in FIG. 11, the gas chamber 320 to which the measurement gas electrode 15 is exposed. The spacer 34 is interposed between the solid electrolyte plate 33 and the heater substrate 14 and has formed therein a longitudinal groove 340 to define a reference gas chamber 120 into which a reference gas such as air is admitted. Other arrangements are identical with those in the first embodiment. The gas sensor element 3 is capable of measuring an air-fuel ratio in automotive engines over a wider range and thus suitable for burning control of the engine requiring fine adjustment of the air-fuel ratio. An operation of this type of gas sensor element is well know in the art, and explanation thereof in detail will be omitted here. For example, U.S. Pat. No. 5,700,367 discloses an operation of a two-cell type gas sensor, disclosure of which is incorporated herein by reference.

We calculated a thermal stress produced in a simulated operation in which the gas sensor element 1 of the first embodiment was heated within five minutes from room temperature up to 600° C. that is an operating temperature of the gas sensor element 1. The calculation was performed for different values of the width C of the gas sensor element 1 from 2.8 mm to 6.2 mm. Calculated thermal stresses are shown in FIG. 12.

Figure 12:
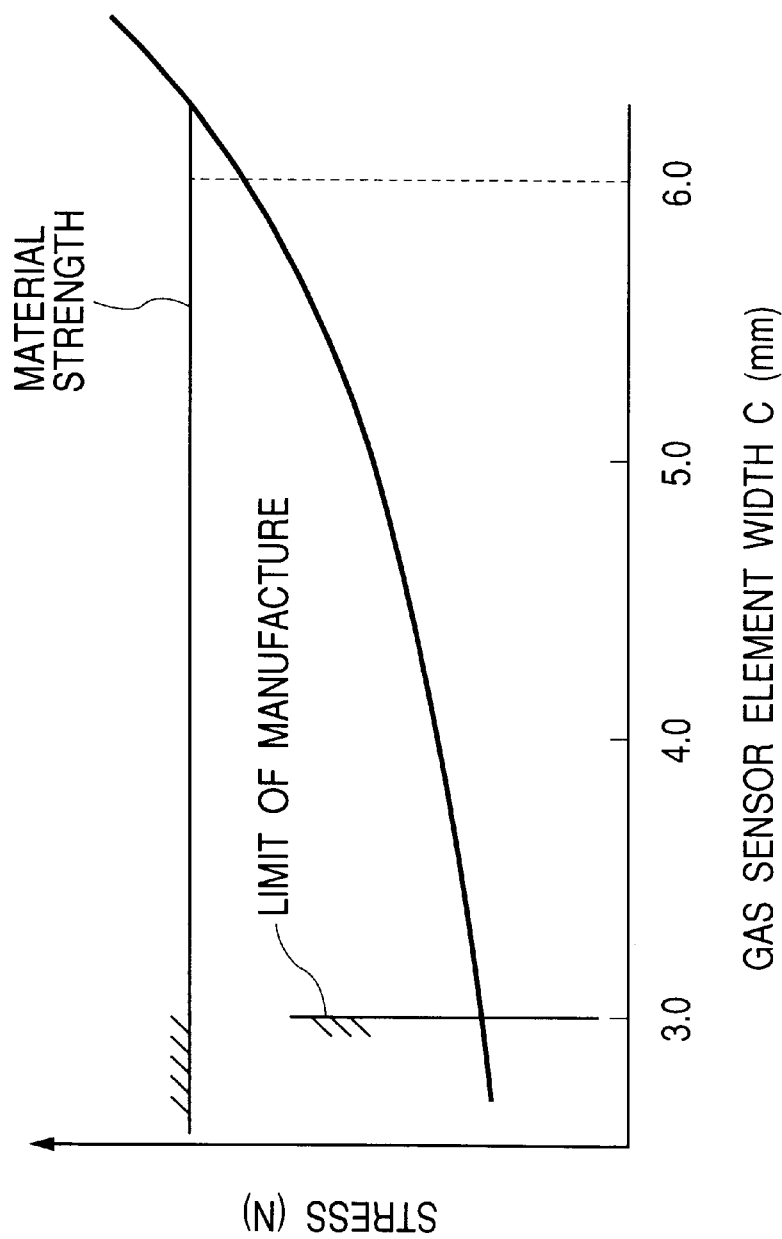
FIG. 12 is a graph which represents a relation between thermal stress and a width C of a gas sensor element.

FIG. 12 shows that the greater the width C, the greater the thermal stress produced in the gas sensor element 1, and when the thermal stress exceeds the strength of material of the heater substrate 14, it will cause cracks to be produced in the heater substrate 14. When the width C of the gas sensor element 1 is smaller than 3 mm, it becomes impossible to provide a greater difference in resistance between the leads 199 and the heating element 19 due to some limits of manufacture. It is, thus, difficult to design the heating element 19 that is excellent in heating efficiency. It is, therefore, found that the width C of the gas sensor element 1 lies preferably within a range of 3 mm to 6 mm.

Figure 13:
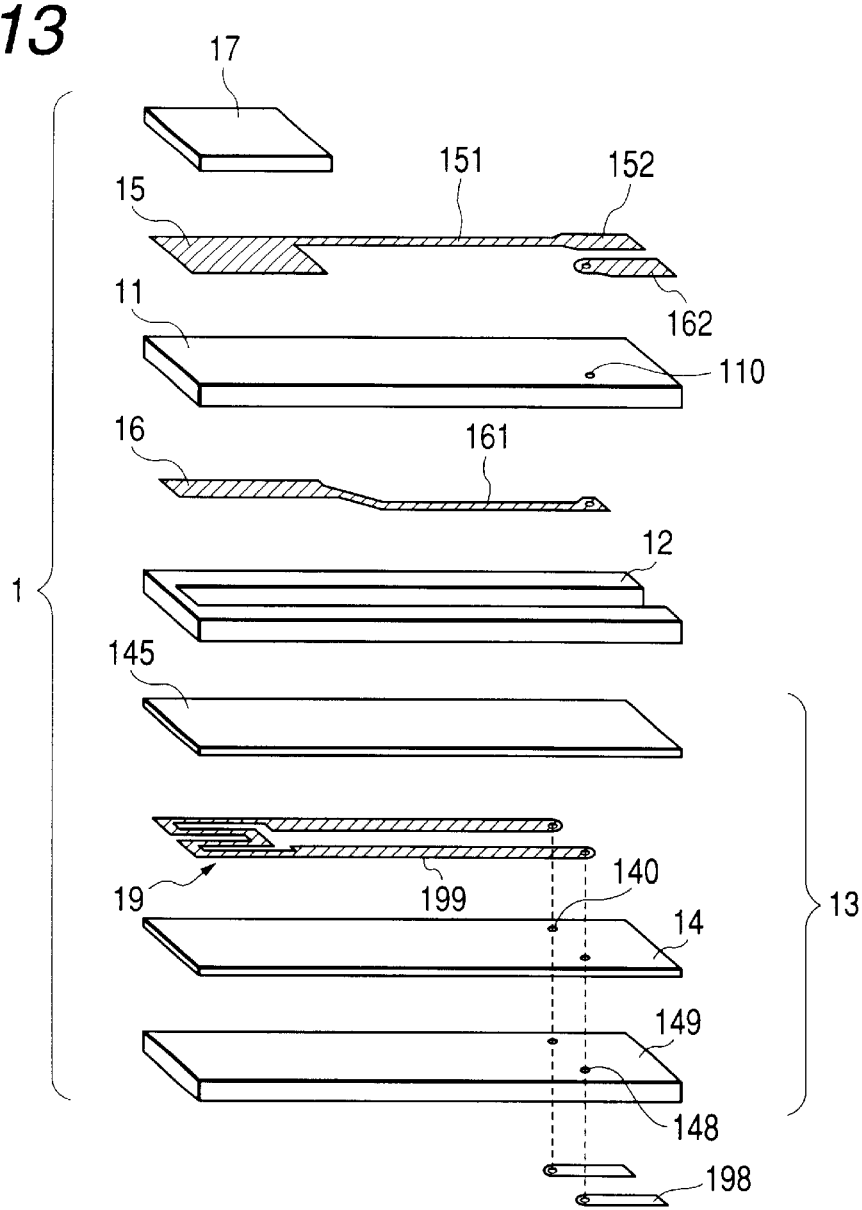
FIG. 13 is an exploded perspective view which shows a gas sensor element according to the fifth embodiment of the invention.
Figure 14:
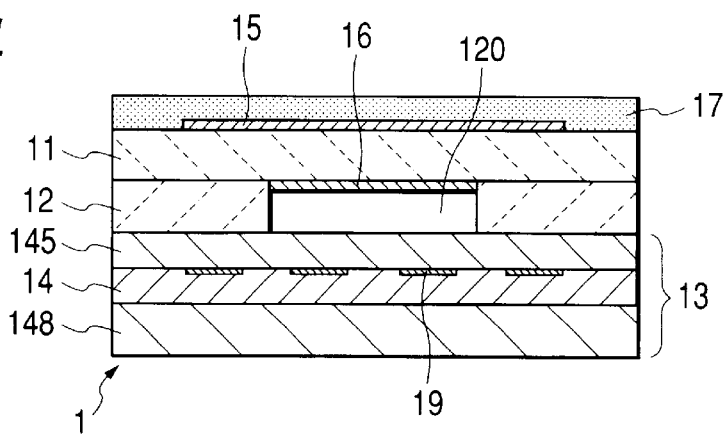
FIG. 14 is a traverse cross section of FIG. 13.

FIGS. 13 and 14 show a gas sensor element 1 according to the fifth embodiment of the invention.

The gas sensor element 1 is made of a lamination of a solid electrolyte plate 11, a spacer 12, and a heater 13. The solid electrolyte plate 11 has formed on a major surface thereof a measurement gas electrode 15 which is covered with a protective film 17. A reference gas electrode 16 is attached to a surface of the solid electrolyte plate 11 which is opposite the measurement gas electrode 15 and exposed to a reference gas chamber 120 defined by a slit formed in the spacer 12.

Output pickup leads 151 and 161 and terminals 152 and 162 are formed on the solid electrolyte plate 11 in electric connection with the measurement gas electrode 15 and the reference gas electrode 16, respectively.

The heater 13 is made of a lamination of a heating element 19 connected to the power supply leads 199 for applying the voltage to the heating element 19, a heater substrate 14, an insulating substrate 145, and a support plate 149. The support plate 149 serves to carry the heating element 19, the heater substrate 14, and the insulating substrate 145. Other arrangements are identical with those in the first embodiment, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas sensor element comprising:

a solid electrolyte member having opposed surfaces; a measurement gas electrode disposed on one of the opposed surfaces of said solid electrolyte member, said measurement gas electrode being exposed to a gas to be measured;

a reference gas electrode disposed on the other of the opposed surfaces of said solid electrolyte member, said reference gas electrode being exposed to a reference gas; and a heater laminated on said solid electrolyte member, said heater including a heater substrate, a heating element, and leads for supplying power to the heating element, the heating element and leads being disposed on the heater substrate, a minimum distance X between an edge of the heater substrate and an edge of the heating element meeting a relation of 0.1 mm≦X≦0.6 mm, wherein the heater substrate and the heating element each have a length, and wherein a minimum distance Y between a tip of the heater substrate and a tip of the heating element meets a relation of 1.0 mm≦Y≦2.5 mm.

2. A gas sensor element as set forth in claim 1, further comprising a reference gas chamber into which the reference gas is admitted and to which said reference gas electrode is exposed, and wherein the reference gas chamber having a length substantially coinciding with a length of the heating element, and a width A of said reference gas chamber and a width B of the heating element meet a relation of A<B.

3. A gas sensor element as set forth in claim 1, wherein the gas sensor element has a width of 3 to 6 mm.

4. A gas sensor element as set forth in claim 1, wherein the gas sensor element is a air-fuel ratio sensor element.

5. A gas sensor element as set forth in claim 1, wherein when the heater is energized by applying 20 volts to the heating element, the resistance of the heating element being controlled to about 20Ω, the substrate is substantially free of cracks after at least about 10 minutes at a heater surface temperature of 1000° C.

6. A gas sensor as claimed in claim 1, disposed in an exhaust system of an automotive engine.

* * * * *